United States Patent [19]

Ragheb

[11] Patent Number: 4,932,422
[45] Date of Patent: Jun. 12, 1990

[54] CONTRACEPTIVE DEVICE

[76] Inventor: Gamal A. Ragheb, 79 Bradstreet Ave., Revere, Mass. 02151

[21] Appl. No.: 364,841

[22] Filed: Jun. 12, 1989

[51] Int. Cl.$^5$ .................. A61F 13/00; A61F 5/00
[52] U.S. Cl. .................. 128/839; 128/840
[58] Field of Search ............. 128/830, 831, 833, 834, 128/835, 836, 837, 838, 839, 840, 841, 842, 844; 604/347–353; 446/224; 210/136

[56] References Cited

U.S. PATENT DOCUMENTS

| | | | |
|---|---|---|---|
| 49,949 | 12/1863 | Scattergood | 128/834 |
| 80,163 | 7/1868 | Gorgas | 128/834 |
| 604,958 | 5/1898 | Biesmeyer | 128/834 |
| 1,083,721 | 1/1914 | Asch | 128/834 |
| 1,219,496 | 3/1917 | Shaulis | 128/834 |
| 1,917,870 | 7/1933 | Bley | 128/841 |
| 2,452,229 | 10/1948 | Bray | 128/834 |
| 2,764,975 | 10/1956 | Greenberg | 128/841 |
| 2,836,177 | 5/1958 | Sells | 128/841 |
| 3,598,115 | 8/1971 | Horne | 128/833 |
| 3,656,483 | 4/1972 | Rudel | 128/840 |
| 3,777,015 | 12/1973 | Zaffaroni | 128/833 |
| 3,952,737 | 4/1976 | Lipfert | 128/841 |
| 4,146,024 | 3/1979 | Shroff | 128/841 |
| 4,246,896 | 1/1981 | Horne | 128/833 |
| 4,276,163 | 6/1981 | Gordon | 210/136 |
| 4,287,917 | 9/1981 | Fray | 210/136 |
| 4,369,219 | 1/1983 | Goepp | 128/841 |
| 4,469,594 | 9/1984 | Poetter | 210/136 |
| 4,614,182 | 9/1986 | Boebel | 128/840 |
| 4,658,810 | 4/1987 | Bauer | 128/839 |
| 4,681,138 | 7/1987 | Giuligni | 446/224 |
| 4,682,592 | 7/1987 | Thorsgard | 128/842 |
| 4,703,752 | 11/1987 | Gabbay | 128/841 |
| 4,711,235 | 12/1987 | Willis | 128/839 |
| 4,832,651 | 5/1989 | Buck | 446/224 |

*Primary Examiner*—Robert A. Hafer
*Assistant Examiner*—Mitchell Brown
*Attorney, Agent, or Firm*—William Nitkin

[57] ABSTRACT

A contraceptive device having a cylindrical body adapted to be retained within the cervix having a valve mechanism adapted to allow passage of menstrual fluid yet blocking seminal fluid.

5 Claims, 2 Drawing Sheets

CONTRACEPTIVE DEVICE

BACKGROUND OF THE INVENTION

1. Field of the Invention

The device of this invention resides in the area of contraceptive devices and more particularly relates to a device which is inserted into the cervix having a "security valve" which allows the escape of menstrual flow but yet blocks semen from entering the uterus through the cervix.

2. Description of the Prior Art

Birth control devices are well known such as interuterine device which are inserted through the cervix, some of which are positioned within the uterus. Many of these devices have drawbacks such as spontaneous expulsion and spontaneous invasion into the uterus requiring surgical removal. Other inconvenient side effects are those such as may be caused by the string members of interuterine devices which must be left extending out of the cervix into the vagina for future removal of the device and which strings can be noticeable during sexual intercourse and may interfere with the physical act.

SUMMARY OF THE INVENTION

It is an object of this invention to provide a new contraceptive device which is introduced into the cervix and utilizes a one-way valve which allows menstrual flow to escape but yet prevents the passage of semen through the cervix. The device of this invention has a cylindrical body and is inserted into the cervix by an inserting applicator. The valve member has a movable flap as will be described further below and hook members at the top which, when the device is inserted through the cervix and withdrawn slightly, hooks to the inner bottom wall of the uterus to retain the "cervical security valve" of this invention in place.

DESCRIPTION OF THE PREFERRED EMBODIMENT(S)

Figure 1:
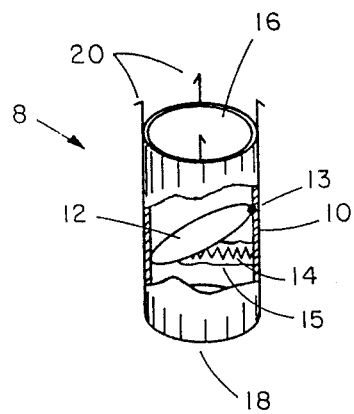
FIG. 1 illustrates a perspective cutaway view of the "cervical security valve" of this invention with its valve member in its closed mode.
Figure 3:
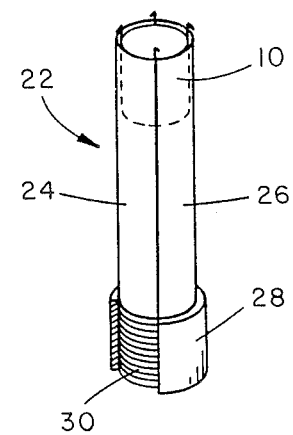
FIG. 3 illustrates a perspective view of the "cervical security valve" of FIG. 1 positioned within its inserting applicator.
Figure 4:
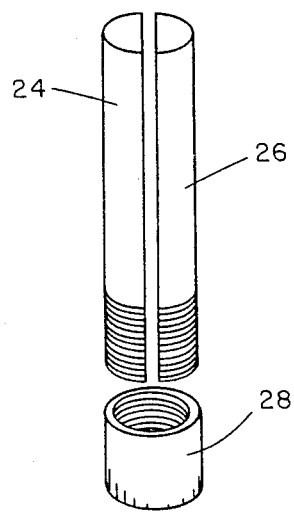
FIG. 4 illustrates a perspective view of the parts of the inserting applicator spaced apart from one another.

FIG. 1 illustrates the "cervical security valve" 8 of this invention consisting of open cylindrical body 10 with a plurality of wire hooks 20 extending from the top thereof. Top 16 and bottom 18 of cylindrical body 10 are open. Contained within cylindrical body 10 is flap member 12 hingeably attached at point 13 to the inside of body 10 and which flap completely extends to block the opening through cylindrical body 10 with spring member 14 biased to push flap 12 in a position whereby it is closed. Spring member 14 is surrounded by a protective flexible sheath 15. Cervical security valve 8 is positioned within the cervix by introducing applicator 22 seen in FIG. 3 which is comprised of two half-cylindrical side members 24 and 26 with retention collar 28 screwed on tapered threads 30 at the bottom of side members 24 and 26 so that when the "cervical security valve" is positioned therein, it is held securely in place. The device is then introduced into the cervix and advanced through the cervix until hook members 20 are beyond the top of the cervix and extend into the uterus. The device is then withdrawn slightly which movement drives hooks 20, which extend upwards and then curve downward toward the exterior of the device, into the bottom wall of the uterus so that the device remains in position within the cervix with the hooks holding it in place as such hooks engage into the uterine wall. In FIG. 4 the elements of introducing applicator 22 are seen with the two side members 24 and 26 separated. Due to tapered threads 30, the more collar 28 is rotated onto threads 30, the tighter side members 24 and 26 are compressed together.

Figure 2:
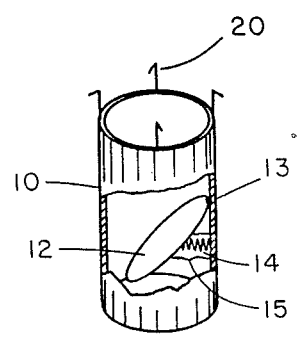
FIG. 2 illustrates a perspective cutaway view of the "cervical security valve" of FIG. 1 with its valve member in its open mode to allow escape of menstrual flow.

In order to allow menstrual flow to escape through the cervix, flap 12, when the flow reaches it, is adapted to move downward on hinge 13 compressing spring 14 as seen in FIG. 2 to allow the menstrual flow to pass through the "cervical security valve" thereby allowing the menstrual flow to escape in its normal fashion. Since flap 12 is elliptical in shape, it only opens downward and is of too large a size to rotate cylinder 8 on its hinge and open upwards in the other direction. Only the slightest pressure from menstrual flow is needed to compress spring 14 to allow the escape of such menstrual flow. When semen is present in the cervix, spring 14 retains flap 12 in a closed position thereby blocking any entrance or passage of the semen through the cervix into the uterus. The "cervical security valve", even under pressure from open end 18, will remain closed as flap 12 cannot open toward open end 18 because of its elliptical shape being longer than the diameter of the cylinder and spring 14 will retain it in a closed position unless there is force against flap 12 from inside the uterus. Flap 12 when closed forms a tight contact seal with the sides of cylindrical body 10.

Figure 5:
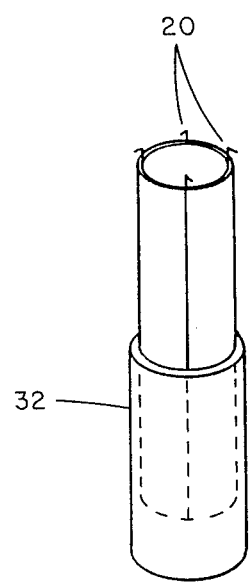
FIG. 5 illustrates a perspective view of parts of the inserting applicator when used for removal of the "cervical security valve" of this invention.
Figure 6:
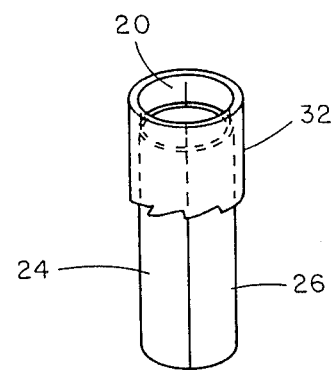
FIG. 6 illustrates a perspective view of parts of the inserting applicator in their mode to disconnect and straighten the hooks from the lower uterine wall when removing the device of this invention.

In order to remove the device of this invention, one can use introducing applicator 22 to grasp around the "cervical security valve" and hold it tightly within said members 24 and 26. Collar 32 seen in FIG. 5 can be pushed up introducing applicator 22 until, as seen in FIG. 6, it lifts and straightens hooks 20 out of the wall of the uterus and then the device can be withdrawn with hooks 20 held within collar 32. Collar 32 is shown shorter than it would be in normal usage. In normal usage it would extend at least the length of the introducing applicator 22 so that it could be maneuvered up and down to cause the release of hooks 20.

The "cervical security valve" of this invention can be approximately one inch in length and can be produced in three diameter sizes such as 5 mms (small), 10 mms (medium), and 15 mms (large). The "cervical security valve" can be made of polyethylene and flap member 12 can be maneuvered by a relatively weak spring 14 to allow it to close automatically with the absence of any pressure from above. The principle utilized here is that the valve only needs a very low pressure to open to allow the menstrual flow to pass outside the cervix, and the flap then will close automatically to prevent any seminal fluids from passing through the cervix to the uterus. The valve, when introduced by the introducing applicator as described above, lies in the cervix and hooks 20 engage into the internal cervico-uterine junction where hooks retain the device in place. Introducing applicator 22 can be held securely by collar 28 which tightens more and more as it is rotated upon threads 30 of the two side members. In one method of application one inserts the device into the vagina with hooks 20 held compressed and hanging over side members 24 and 26 of the introducing applicator until it is inside the interuterine cavity. One then opens the introducing applicator by rotating collar 28 thereby allowing the collapsed hooks 20 to spread outward from their retained position. One then can slightly retract and then retighten the introducing applicator and pull the "cervical security valve" downward to cause hooks 20 to engage into the internal wall of the cervico-uterine junction and then again widen the introducing applicator side members 24 and 26 again to pull it out of the cervix, leaving the "cervical security valve" in place within the cervix.

Figure 7:
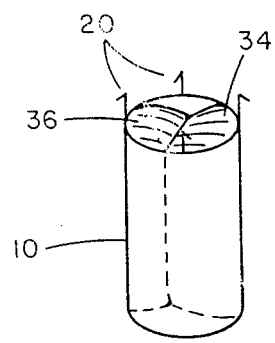
FIG. 7 illustrates a perspective view of an alternate embodiment of the device of this invention with a modified valve mechanism.
Figure 8:
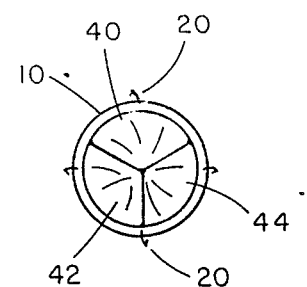
FIG. 8 illustrates a top view of the deivce of this invention having a three-cusp valve.
Figure 9:
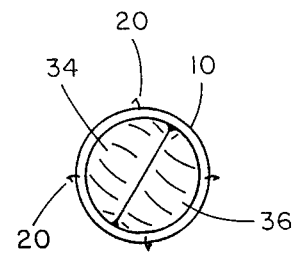
FIG. 9 illustrates a top view of the device having a two-cusp valve.

Other internal valve mechanisms could be utilized in place of flap 12. One such valve is illustrated in FIGS. 7 and 9 and has two cusp members 34 and 36 made from a polyethylene material with an internal spring member, not illustrated, located within each section urging them together which valve also requires only a low pressure to open it to allow menstrual flow to pass from the uterus outside. Such valve, though, prevents seminal fluid from entering because its closing pressure is still greater than the negligible pressure of the seminal fluid. The pressure of the seminal fluid being negligible when compared to the pressure of the menstrual fluid cannot open the cusps of the valves illustrated in FIGS. 7, 8 and 9 and therefore they block passage of the seminal fluid and only allow the menstrual flow. This valve can also be made in three sections as seen in FIG. 8 where cusps 40, 42 and 44 will also open with slight pressure from above but will prevent seminal fluid from entering from below.

Figure 10:
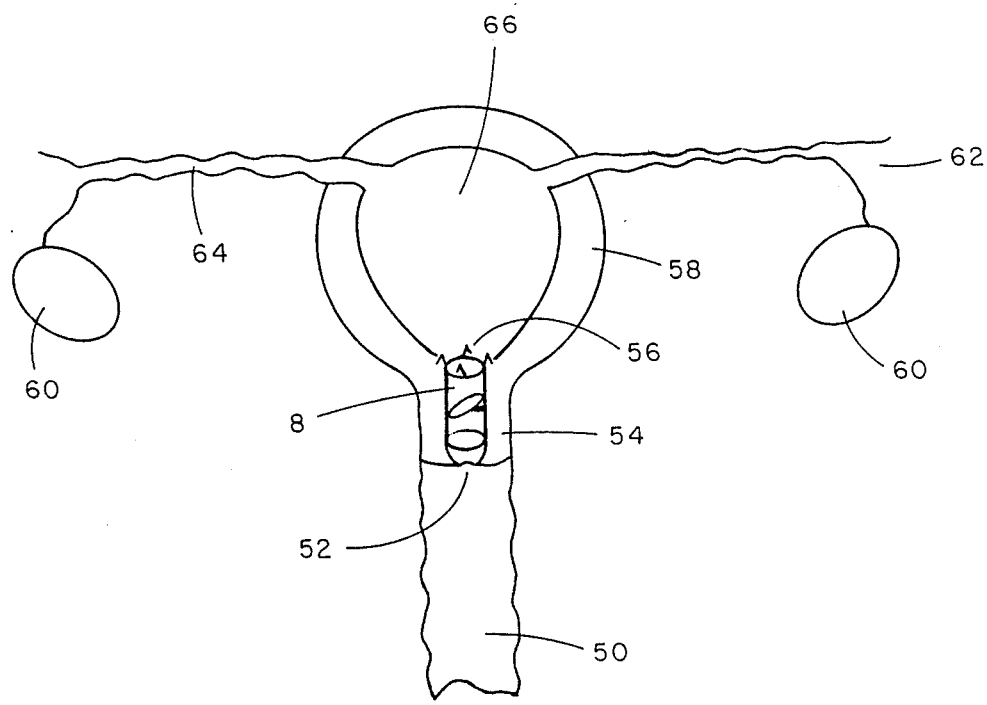
FIG. 10 illustrates a cutaway view of the "cervical security valve" of this invention in place in the cervix.

FIG. 10 illustrates the "cervical security valve" 8 in place in cervix 54 above vagina 50. Seminal fluid might pass through cervical opening 52 but cannot get past "cervical security valve" 8. "Cervical security valve" 8 is shown with its hooks engaged into the cervico-uterine junction 56. Menstrual flow from uterine cavity 66 can escape through the "cervical security valve" 8. Also seen in this view are ovaries 60, Fallopian tube 64, cone 62 of the tube, uterine wall 58, and uterine cavity 66 illustrating the anatomy of the female reproductive system.

Although the present invention has been described with reference to particular embodiments, it will be apparent to those skilled in the art that variations and modifications can be substituted therefor without departing from the principles and spirit of the invention.

I claim:

1. A contraceptive device comprising:
   an open cylindrical body having upper and lower ends, said body adapted for insertion in the cervix with its sides contacting the sides of the cervix preventing fluid passage therebetween;
   retention means to retain said cylindrical body in position in the cervix said retention means having a plurality of wires extending from the upper end of said cylindrical body, said wires bending outward and downward to form hooks which are adapted to be engaged in the cervico-uterine junction;
   valve means to allow passage of menstrual fluid through said cylindrical body, said valve means further adapted to block passage of semen to the uterus, said valve means having an elliptical flap hingeably attached within said cylindrical body, said flap extending downward adapted in a first mode to be urged against the inside walls of said cylindrical body; and
   a spring member adapted to urge said flap against the walls of said cylindrical body, said spring member having only sufficient force to hold said flap in a closed first mode, said spring member being further adapted to compress and allow said flap to open upon slight pressure from menstrual fluid from above, said flap adapted to remain in a closed mode when pressured from below to block semen flow coming from the lower end of said cylindrical body.

2. The device of claim 1 further including a protective flexible sheath disposed around said spring member.

3. The device of claim 1 further including an insertion applicator with means to pass around and hold said cylindrical body facilitating insertion into the cervix with means to release said applicator from said cylindrical body once said cylindrical body is positioned in the cervix.

4. A contraceptive device comprising:
   an open cylindrical body having upper and lower ends, said body adapted for insertion within the cervix with its sides contacting the sides of the cervix preventing fluid passage therebetween;
   retention means to retain said cylindrical body in position in the cervix said rotation means having a plurality of wires extending from the upper end of said cylindrical body, said wires bending outward and downward to form hooks which are adapted to be engaged in the cervico-uterine junction;
   valve means to allow passage of menstrual fluid through said cylindrical body, said valve means further adapted to block passage of semen to the uterus, said valve means having at least two facing cusp-shaped members disposed within said cylindrical body; and
   means to urge said cusp-shaped members toward one another to contact one another, said means disposed in each cusp-shaped member and said means having sufficient force to cause said cusp-shaped members to remain closed to block seminal flow but having a force less than the pressure of menstrual flow to allow such menstrual flow to open said cusp-shaped members and to pass through said cylindrical body.

5. The device of claim 4 further including an insertion applicator with means to pass around and hold said cylindrical body facilitating insertion into the cervix with means to release said applicator from said cylindrical body once said cylindrical body is positioned in the cervix.

* * * * *